(12) United States Patent
Maier et al.

(10) Patent No.: US 6,956,029 B1
(45) Date of Patent: Oct. 18, 2005

(54) SOLID FORMULATION OF GLUCOSAMINE SULPHATE

(75) Inventors: Hans-Jürgen Maier, Wald-Oberholz (CH); Harish Parekh, Au/ZH (CH)

(73) Assignee: SCA Lohnherstellungs AG, Kirchberg (CH)

( * ) Notice: Subject to any disclaimer, the term of this patent is extended or adjusted under 35 U.S.C. 154(b) by 0 days.

(21) Appl. No.: 09/926,821

(22) PCT Filed: Jul. 2, 1999

(86) PCT No.: PCT/CH99/00289

§ 371 (c)(1),
(2), (4) Date: Sep. 30, 2002

(87) PCT Pub. No.: WO01/01992

PCT Pub. Date: Jan. 11, 2001

(51) Int. Cl.[7] .......................................... A61K 31/7008

(52) U.S. Cl. ........................... 514/62; 424/44; 424/46; 424/466

(58) Field of Search ........................... 514/62; 424/44, 424/46, 466

(56) References Cited

U.S. PATENT DOCUMENTS

| 3,683,076 | A | * | 8/1972 | Rovati et al. ................. 514/62 |
| 4,642,340 | A | | 2/1987 | Senin et al. |
| 5,171,571 | A | * | 12/1992 | Stephan et al. ............. 424/736 |
| 5,843,923 | A | * | 12/1998 | Schleck et al. ............... 514/62 |

FOREIGN PATENT DOCUMENTS

| CH | 525 861 | | 9/1972 | |
| EP | 214642 | | 3/1987 | |
| EP | 444000 | | 8/1991 | |
| EP | 0444000 | * | 8/1991 | .......... A61K 31/70 |
| JP | 011092385 | | 4/1999 | |
| JP | 11092385 | * | 4/1999 | .......... A61K 31/70 |
| WO | WO 99/04765 | * | 2/1999 | ............ A61K 9/46 |

* cited by examiner

*Primary Examiner*—James O. Wilson
*Assistant Examiner*—Ganapathy Krishnan
(74) *Attorney, Agent, or Firm*—Shoemaker and Mattare

(57) ABSTRACT

An effervescent preparation of glucosamine sulfate or a mixed salt thereof, suitable for preparing a drinkable medicine and applying a patient's daily dosage in a single dose. In a preferred embodiment of the invention, the preparation comprises a fruit acid, preferably citric acid, as acid component and for the improvement of storage-stability. A further preferred dosage form is effervescent tablets.

20 Claims, No Drawings

SOLID FORMULATION OF GLUCOSAMINE SULPHATE

The present invention relates to a solid formulation of glucosamine sulphate or a mixed salt thereof in accordance with the preamble of claim 1. Glucosamine sulphate is a well-known substance for the treatment of rheumatic fever, pains resulting from arthrosis and arthritis and generally of all pathological conditions originating from metabolic disorders of the osteo-articular tissue. D-Glucosamine as the active pharmaceutical compound, used in the form of a salt formed by mixing the amine with sulphuric acid, is known to combine favourable pharmaco-kinetics with its anti-inflammatory effect (for ref., cp. e.g. Setnikar et al., 'Pharmacokinetics of Glucosamine in the Dog and in Man', Arzneimittelforschung, April 1986, 36 (4), pp. 729–735). Methods for industrial synthesis of glucosamine sulphate are described in U.S. Pat. No. 3,683,076 and CH 525861.

However, glucosamine sulphate has several drawbacks as a pharmaceutical compound. Solid glucosamine sulphate is highly hygroscopic and its amino group oxidises readily. Up to now glucosamine sulphate only exists in the form of coated tablets, ampules or capsules and thus is protected from contact to oxygen. The dosage of glucosamine sulphate required for treatment is considerable: The patient has to swallow three times a day 1–2 of the currently available pills, comprimates or capsules, each one comprising roughly 250 mg glucosamine sulphate. In contrast, parentally applied pharmaceutical compositions of glucosamine sulphate allow to provide more than a day's dose by a single injection, though they have the disadvantage that they need to be applied by a physician and that they require local anesthesia.

Thus achieving a convenient dosage form of glucosamine sulphate is a prerequesite for therapeutic compliance.

U.S. Pat. No. 4,642,340 describes formation of a crystalline mixed salt of glucosamine sulphate with an alkali halide, namely sodium chloride. Formation of a mixed salt increases the chemical stability at ambient temperature and renders the glucosamine sulphate less hygroscopic.

EP-214642 describes an improved method for formation of a mixed salt of glucosamine sulphate with alkali halides. Specifically it describes preparation of a mixed salt with potassium chloride. The potassium salt has the advantage of avoiding the disfavourable adiuretic effect of sodium chloride which is particularly detrimental in case of patients with cardio-vascular disease. The mixed salt is essentially stable over 30 days at 75% rH/20° C.

EP-444000 describes the stabilisation of an oral dosage form of glucosamine sulphate by providing ascorbic acid as an anti-oxidant in an amount being of at least ¼ of that of glucosamine sulphate. Calcium carbonate is required as a desiccant. The formulation is suited for manufacturing oral dosage forms such as tablets, most preferably capsules.

However, reducing agents such as ascorbic acid may be prone to slow oxidation and discoloration during storage. Given the increased bulk volume of the formulation, tablets or capsules can not comprise a patient's one-day-dose of glucosamine sulphate.

It is an object of the present invention to overcome the drawbacks of the prior art and provide a formulation of glucosamine sulphate and its mixed salts suitable for preparing a drinkable medicine.

It is a further object of the present invention to provide a pharmaceutical composition destined for oral intake which comprises a one-day-dose of glucosamine sulphate or a mixed salt thereof. This objects are solved with the features of the independent claim 1.

According to the present invention, a solid formulation of glucosamine sulphate or a mixed salt thereof is comprised in an effervescent preparation.

In the context of the present invention, the isolated, solid glucosamine sulphate or mixed salt thereof requires an ambient relativ humidity not greater than 30%, preferably not greater than 10%, and even more preferably not greater than 8% prior to or while preparing the formulation in accordance with the present invention. An ultra-brief wetting step in a flow or spray dryer may be included in the manufacture of a specific dosage form of the formulation. In contrast, with regard to the final, storage-stable formulation, 'solid' refers to standard conditions.

The term "solid" stands for solids as defined in Römpp Chemie Lexikon, Eds. J. Falbe, Dr. Regitz, 9 edition, Georg Thieme Verlag, Stuttgart, N.Y., 1990, S. 1334.

Prior art does not yet provide glucosamine sulphate or a mixed salt thereof in a drinkable, especially not in an effervescent formulation. An effervescent preparation or effervescent tablet simplifies the preparation of a potable medicine by dissolving a storage-stable, solid formulation of glucosamine sulphate or a mixed salt thereof in liquid. Given the large doses required for treatment, an effervescent preparation is the ideal mode of applying the medicine and there is no pharmaceutical objection withstanding. An effervescent preparation usually comprises $CO_3^{2-}$ or $HCO_3^{-}$-salts in the presence of an acid, the latter also being provided in the form of a solid; upon dissolution in water, gas ($CO_2$) is generated. ("Brausetabletten, eine Arzneiform", P. C. Schmidt, I. Christin, Die Pharmazie/Organ der Pharmazeutischen Gesellschaft No. 45, p. 89, 1990). Additional ingredients such as flavourants, colourants, fillers, manufacturing auxiliaries, anti-oxidants etc. can be comprised in an effervescent preparation in accordance with the present invention. A prefered embodiment of an effervescent preparation according to the present invention are effervescent tablets.

An effervescent preparation has the appearance of loose or compressed powder or granules; it is equally possible to additionally provide a protective, easily water-soluble coating or a means for separate packaging to improve storage-stability. The bicarbonate or carbonate included in an effervescent preparation likewise will function as an additional desiccant during storage. The carbonat can be provided in a large amount, due to the packaging as an effervescent preparation (or effervescent tablet). This does not impose a size-limit as does the conventional packaging in dosage forms that are destined for direct oral intake, i.e. that are swallowed as such, for instance pills, comprimates or capsules.

A further prefered embodiment of the present invention is a packaging of a patient's complete daily dosage of glucosamine sulphate in a single dose of the aforementioned storage-stable, solid formulation, destined for preparing a drinkable medicine. A patient's recommended daily dosage is in the range of approximately 700–1500 mg glucosamine sulphate per day, though this is an average which may be exceeded for certain individuals. That amount is easily contained in an (effervescent) preparation, but not in a conventional pill.

In a prefered embodiment of the present invention, an effervescent formulation of glucosamine sulphate or a mixed salt thereof comprises a fruit acid. The fruit acid is homogenously mixed with the glucosamine sulphate or a mixed salt thereof. The fruit acid provides the acidity required to extrude carbon dioxide upon dissolving the effervescent preparation in water and, surprisingly, also enhances the storage-stability of a solid formulation of glucosamine sulphate or a mixed salt thereof. In addition, the fruit acid, most preferably citric acid, provides a favorable taste to the drink.

'Fruit acid' (acc. to Römpp Chemie Lexikon, ed. J. Falbe, M. Regitz, Thieme Verlag, Stuttgart/N.Y. 1990) is a common generic term for bio-compatible carboxylic acids naturally occuring in fruits. Examples are citric acid, tartric acid, glutaric, lactic, malic or gluconic acid. Fruit acids are common additives in nutrition; food chemists also refer to them as 'food acids' and use them for preservation or flavoring of nutritionals. They may naturally occur in a wide concentration range. Some such as citric or malic acid are abundant both in fruits and vegetables, whereas some as glutaric acid are naturally only occuring in certain vegetables in larger amounts. The majority of fruit acids is found in what is considered a fruit (tables in: Food chemistry, H. D. Belitz, W. Grosch, Springer Verlag 1987), namely a seed (the zygote) surrounded by a shell or peel. This definition includes vegetables, corns, fruits, etc. In a prefered embodiment fruits are citrus fruits.

Fruit acids in accordance with the present invention are all aliphatic carboxylic organic acids satisfying the above mentioned definition. In the context of the present invention, the term aliphatic encompasses linear and/or branched as well as ali- and/or heterocyclic saturated compounds. Besides the carboxylic groups they may bear other unsaturated functional groups. In a prefered embodiment the fruit acids have linear saturated C-chains. Thus all carboxylic organic acids having unsaturated C-chains such as ascorbic acid are excluded. Therefore fruit acids employed in the present invention do not display the reactivity typical for olefinic bonds and are therefore more stable upon storage. Whilst not intending to provide a complete theory for the stabilizing effect of the fruit acid, fruit acids encompassed by the definition of the present invention are strongly acidifying (tartric acid $pK_{a1}$:2.9; citric acid $pK_{a1}$:3.1 as compared to ascorbic acid $pk_{a1}$:4.1). The pH of an aequeous solution is an important parameter for oxidation reactions, as is well known to chemists. The electrochemical potential, as expressed by the Equation of Nernst, can be a function of the concentration of $H^+$ or $H_3O^+$, respectively. In a solid formulation according to the present invention, ambient humidity may temporarily hydratize or dissolve microscopic domains in that formulation. A pH in the range of pH 3–4, preferably of at least pH 3, is then favourable in order to prevent oxidation of the glucosamine sulphate and is not yet detrimental to the compound itself. It is also conceivable that the fruit acid forms a mixed salt with glucosamine sulphate upon transient humidification. The fruit acids in accordance with the present invention are readily water soluble and are therefore ideally suited for those oral dosage forms that need to be dissolved in water prior to consumption, such as an effervescent preparation.

In a prefered embodiment, fruit acids in accordance with the present invention are hydroxylated. They are more readily water-soluble and are more acidic, as judged by their $pk_{a1}$ values, due to the polarizing effect of the hydroxy groups. This latter effect is most pronounced in case of the alpha-carbon atom (with regard to a carboxylic group) carrying a hydroxy group. Furthermore, their multiple polar groups render them effective chelating agents for metal ions which may otherwise serve as catalysts for oxidation reactions or may induce precipitation of other compounds upon dissolving the formulation in water.

In a prefered embodiment of the invention the weight ratio between the solid glucosamine sulphate or a mixed salt thereof and the fruit acid in the solid formulation is in the range of between 0.2:1 to 5:1, preferably in the range of between 0.2:1 to 2:1, and most preferably in the range of between 0.5:1 to 1:1.0. Since always only one or two carboxyl groups per molecule contribute to the initial strong acidity, a large amount of fruit acid provides sufficient buffer capacity and ensures maintenance of a pH in the order of 3–4, preferably around 3.

Preferably the fruit acid in accordance with the present invention has at least two carboxylic groups, since this increases the overall buffer capacity of a formulation comprising that fruit acid, renders it more acidic due to the polarizing effect of a second carbonyl moiety and renders it a more effective chelating agent.

The prefered fruit acid in accordance with the present invention is citric acid, due to its pharmacological compliance, its excellent solubility (62 g/l) in water, its strong acidity ($pK_{a1}$:3.1) and its chelating properties.

Preferably, the fruit acid is pure, crystalline citric acid as specified in the European Pharmacopeia. In an even more prefered embodiment of the present invention, the fruit acid is anhydrous, crystalline citric acid. 'Anhydrous' refers to a water content of crystalline citric acid of or of less than 0.5% as specified in the European Pharmacopeia. This ensures minimal hygroscopicity and maximum stability of the citric acid in a storage-stable formulation with glucosamine sulphate or a mixed salt thereof. Both the monohydrate and anhydrous crystalline citric acid have well-defined crystal geometries and are stable when stored at standard relative humidity. The monohydrate is modifying at a temperature beyond 75° C., whereas the anhydrous form remains solid ard chemically stable up to 153° C.

In a prefered embodiment of the present invention, the mixed salt of glucosamine sulphate employed in a formulation according to the present invention is either glucosamine sulphate 2 KCl or glucosamine sulphate HCl. As known from prior art, the manufacture of a mixed salt of glucosamine sulphate having inorganic ions such as $K^+$ as cation is well-known in the art and has the advantage of reducing hygroscopicity as compared to the bare glucosamine sulphate; a variety of halide salts can be employed in the manufacture of a mixed salt of glucosamine sulphate. A formulation in accordance with the present invention employing a mixed salt of glucosamine sulphate combines the advantageous, stabilizing effect of the mixed salt and of the fruit acid. However, a potassium or hydro chloride mixed salt is preferable to a sodium salt due to the adverse adiuretic effect of the latter, especially for patients with cardiovascular disease.

In another prefered embodiment, a formulation in accordance with the present invention comprises an anti-oxidant, preferably up to 5% (w/w). Thus the formulation comprises an additional protective agent against oxidation acting synergistically with the fruit acid.

In another prefered embodiment, a formulation according to the present invention is characterized in that the production method comprises the step of spraying a mixture, comprising at least glucosamine sulphate or a mixed salt thereof and a fruit acid, preferably citric acid, with water in a spray dryer prior to drying the complete formulation to a water content of less than 1.5% (W/W). The granulation step in a spray dryer (fluid bed granulator) provides transiently the humidity to the mixture.

EXAMPLE 1

Glucosamine Sulphate Effervescent Tablets With Lemon Flavour, Total Weight 4.5 g Recommended daily dosage: ~750 mg D-glucosamine sulphate D-glucosamine sulphate di-potassium chloride is mixed with the acidic ingredients, the colorants and the flavor additives in a mixed-flow spray dryer; addition of sprayed water leads to formation of granules. In parallel, the basic ingredients are mixed alike. Both granular pre-mixes are joined and mixed in the mixed-flow spray dryer. The composition thus obtained is compressed to biplanar tabletts of 25 mm diameter (thickness: 6 mm) on a high-speed tabletting machine. A tube made of non-transparent PET is used for packaging the tablets in lots of twenty.

| | |
|---|---|
| D-glucosamine sulphate.2KCl | 750 mg |
| Citric acid | 1662.5 mg |
| Maltodex | 270 mg |
| Sorbitol powder | 13.5 mg |
| Saccharine | 15 mg |
| Sodium carbonate 0–50 | 1124 mg |
| Colourant | 30 mg |
| Lemon flavor | 635 mg |

EXAMPLE 2

Glucosamine Effervescent Tablets with Orange Flavour, Total Weight 6.5 g

Recommended daily dosage: 1500 mg D-glucosamine sulphate

The manufacture of the tabletts is identical to the procedure as described in example 1.

| | |
|---|---|
| D-glucosamine sulphate.HCl | 1500 mg |
| Citric acid | 1933 mg |
| Maltodex | 390 mg |
| Sorbitol powder | 19.5 mg |
| Saccharine | 15 mg |
| Sodium carbonate 0–13 | 1517.5 mg |
| Colourant | 5 mg |
| Aromes | 1120 mg |

What is claimed is:

1. A solid formulation of glucosamine sulphate or a mixed salt thereof, in an effervescent preparation.
2. A formulation according to claim 1, wherein the formulation comprises 500–2000 mg glucosamine sulphate or a mixed salt thereof in a single dose.
3. A formulation according to claim 1, wherein the formulation comprises 750–1500 mg glucosamine sulphate or a mixed salt thereof in a single dose.
4. A formulation according to claim 1, further comprising a fruit acid for improving storage stability.
5. A formulation according to claim 4, wherein the weight ratio of the glucosamine sulphate or a mixed salt thereof to said fruit acid is from 0.2:1 to 5:1.
6. A formulation according to claim 4, wherein the weight ratio of the glucosamine sulphate or a mixed salt thereof to said fruit acid is from 0.2:1 to 2:1.
7. A formulation according to claim 4, wherein the weight ratio of the glucosamine sulphate or a mixed salt thereof to said fruit acid is from 0.5:1 to 1:1.
8. A formulation according to claim 4, wherein said fruit acid is hydroxlyated.
9. A formulation according to claim 4, wherein said fruit acid is an aliphatic carboxylic organic acid.
10. A formulation according to claim 4, wherein said fruit acid is selected from the group consisting of citric, tartaric, glutaric, lactic, malic and gluconic acids.
11. A formulation according to claim 4, wherein said fruit acid has at least two carboxylic groups.
12. A formulation according to claim 4, wherein said fruit acid is citric acid.
13. A formulation according to claim 4, wherein said fruit acid is crystalline citric acid.
14. A formulation according to claim 4, wherein said fruit acid is anhydrous.
15. A formulation according to claim 1, wherein the mixed salt is a glucosamine sulphate hydrochloride.
16. A formulation according to claim 1, wherein the mixed salt is a glucosamine sulphate potassium chloride.
17. A formulation according to claim 1, further comprising an anti-oxidant.
18. A formulation according to claim 1, produced by a method comprising steps of
spraying a mixture of glucosamine sulphate or a mixed salt thereof and a fruit acid with water in a spray dryer, and then
drying the formulation to a water content of at most 1.5% by weight.
19. A formulation according to claim 18, wherein said water content is at most 0.5% by weight.
20. A formulation according to claim 18, wherein said fruit acid is citric acid.

* * * * *